US00PP28720P3

(12) United States Plant Patent
Bédard

(10) Patent No.: US PP28,720 P3
(45) Date of Patent: Dec. 5, 2017

(54) GRANDIFLORA ROSE PLANT NAMED 'WEKPURMEBEP'

(50) Latin Name: *Rosa hybrida*
Varietal Denomination: WEKpurmebep

(71) Applicant: Early Morning LLC, Lawrenceburg, IN (US)

(72) Inventor: Christian Bédard, Placentia, CA (US)

(73) Assignee: Early Morning LLC, Lawrenceburg, IN (US)

( * ) Notice: Subject to any disclaimer, the term of this patent is extended or adjusted under 35 U.S.C. 154(b) by 63 days.

(21) Appl. No.: 14/757,088

(22) Filed: Nov. 16, 2015

(65) Prior Publication Data

US 2017/0142879 P1 May 18, 2017

(51) Int. Cl.
*A01H 5/02* (2006.01)

(52) U.S. Cl.
USPC ..... Plt./132

(58) Field of Classification Search
USPC ..... Plt./132, 130, 131, 142, 141, 143, 137, Plt./133, 102
CPC ..... A01H 5/0222; A01H 5/02; A01H 5/00; A01H 5/0216
See application file for complete search history.

(56) References Cited

PUBLICATIONS

Edmunds' Roses Miss Congeniality Grandiflora Rose retrieved on Mar. 6, 2017, retrieved from the Internet at https://www.edmundsroses.com/P/23997/Miss+Congeniality+Grandiflora+Rose 2 pp.*

Houzz Garden Web Jul. 2015 Miss Congeniality, retrieved on Mar. 6, 2017, retrieved from the Internet at <http://forums2.gardenweb.com/discussions/3264649/miss-congeniality> 3 pp.*

* cited by examiner

*Primary Examiner* — June Hwu
(74) *Attorney, Agent, or Firm* — McKee, Voorhees & Sease, PLC

(57) ABSTRACT

A new variety of Grandiflora rose suitable for garden decoration, having flowers of white edged pink coloration.

1 Drawing Sheet

Classification: The present invention relates to a new *Rosa hybrida* plant.

Variety denomination: The new plant has the varietal denomination 'WEKpurmebep'.

BACKGROUND OF THE INVENTION

This invention relates to a new and distinct variety of Grandiflora Rose. It has an unnamed, non-disseminated seedling of my creation as its seed parent with the following genetic origin {[(International Herald Tribune×*Rosa soulieana* derivative)×(Sweet Chariot×Blue Nile)]×(Blueberry Hill×Stephen's Big Purple)} and an unnamed, non-disseminated seedling of my creation as its pollen parent with the following genetic origin (Meredith×Betty Boop).

SUMMARY OF THE INVENTION

Among the features which distinguish the new variety from other presently available and commercial rose cultivars known to the inventor are the following combinations of characteristics: its excellent color stability throughout the life of the flower, its many stipitate glands and numerous hairs on the peduncle, its many stipitate glands on the branches and its occasional nine leaflets. The plant has an upright moderately spreading growing habit, suitable for outdoor garden decoration.

Asexual reproduction of the new variety by T-budding as performed in Kern County and Pomona, Calif., shows that the foregoing and other distinguishing characteristics come true to form and are established and transmitted through succeeding asexual propagations. 'WEKpurmebep' may be asexually propagated by cuttings, budding and grafting. The budding and grafting successfully occurred on the plant/rootstock *Rosa hybrida* 'Dr. Huey' (not patented).

COMPARISON WITH PARENTS

The new rose may be distinguished from its seed parent, a non-disseminated seedling of my creation by the following combination of characteristics: whereas 'WEKpurmebep' bears double flowers (about 20 to 30 petals) of white edged pink coloration, the non-disseminated seedling bears very double flowers of red-purple with a lavender eye coloration with significantly heavier petalage (about 35 to 42 petals). The new variety has a moderate sweet pear with slight spicy fragrance, whereas the seed parent has a strong citrus blossom and rose fragrance.

The new variety may be distinguished from its pollen parent, a non-disseminated seedling of my creation by the following combination of characteristics: whereas 'WEKpurmebep' bears double flowers (about 20 to 30 petals) of white edged pink coloration, the non-disseminated seedling bears semi-double flowers of white with a coral orange edge coloration with significantly lesser petalage (about 15 to 20 petals). The new variety has an upright moderately spreading medium height to somewhat tall growing habit (about 128 to about 175 cm. in height), whereas the pollen parent has a rounded compact significantly shorter growing habit (about 70 to about 85 cm. in height).

COMPARISON WITH THE CLOSEST COMMERCIALLY AVAILABLE CULTIVAR

The new variety may be distinguished from its closest commercially available cultivar, 'KORweiso' (not patented) by the following combination of characteristics: whereas 'WEKpurmebep' bears double flowers (about 20 to 30 petals) of white edged pink coloration, 'KORweiso' bears semi-double flowers of white edged with dark pink to light red coloration with significantly lesser petalage (up to 20 petals). The new variety averages about 55 stamens, whereas the closest commercially available cultivar averages about 30 stamens. The new variety has an upright moderately spreading medium height to somewhat tall growing habit (about 128 to about 175 cm. in height), whereas the closest commercially available cultivar has an upright significantly taller growing habit (about 150 to about 215 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, usually in clusters of two to five or more per stem. Flowers may be borne in regular rounded clusters on strong medium to somewhat long stems (about 28 to about 82 cm.). The cluster ranges from about 11.7 to about 17.4 cm. in diameter. Outdoors, the plant blooms abundantly and nearly continuously during the growing season. The flowers have a moderate sweet pear with slight spicy fragrance.

BUD

The peduncle is about 2.6 to about 6.6 cm. in length, of average caliper (about 0.2 to about 0.3 cm. in diameter), and usually erect to somewhat stiff. It is moderately rough, with many stipitate glands and numerous hairs. Peduncle color is between 146C and 146B sometimes lightly suffused, especially on the side exposed to the sun, with near 187B.

Before the calyx breaks, the bud is about 1.1 to about 1.5 cm. in diameter at the widest point, about 1.4 to about 2.0 cm. in length, and pointed to somewhat ovoid in shape. The surface of the bud bears between 11 to 14 foliaceous appendages with very few stipitate glands and some hairs, usually with slender entire foliaceous parts extending beyond the tip of the bud about ¼ or more of its length. Bud color is between 137D and 144A sometimes lightly suffused, especially on the side exposed to the sun, with near 187B.

The five sepals are about 2.0 to about 3.2 cm. in length and about 0.7 to about 1.0 cm. in width at the widest point. The outer surface color of the sepal is between 137D and 144A sometimes lightly suffused, especially on the side exposed to the sun, with near 187B. The outer surface of the sepal is smooth and bears between 0 to 6 foliaceous appendages with very few stipitate glands and some hairs. The inner surface color of the sepal is near 138A broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with many stipitate glands and hairs.

The receptacle of the flower is of somewhat short length (about 0.3 to about 0.5 cm.) and average in caliper (about 0.5 to about 0.7 cm. in diameter). The receptacle is urn-shaped in form. Its surface is smooth with some hairs and with moderately thick fleshy walls. The receptacle color is between 146C and 144A sometimes lightly suffused, especially on the side exposed to the sun, with near 187B. As the petals open (after the calyx breaks), the bud is about 1.4 to about 2.2 cm. in diameter at the widest point, about 1.8 to about 2.7 cm. in length, and pointed to moderately ovoid in form. The color of the under surfaces of the newly opened petals is between 154D and 150D at the base gradually suffusing toward the middle of the petal to near 27A blushed with between 60B and 53B to as dark as between 187A and 187B toward the petal edge. There is no visible change in coloration at the point where the petal attaches. The color of the upper surfaces of the newly opened petals is between 154D and 150D at the base gradually suffusing toward the middle of the petal to near 37C blushed with between 60B and 53B toward the petal edge. There is no visible change in coloration at the point where the petal attaches.

BLOOM

When fully open, the bloom ranges from about 7.5 to about 11.2 cm. in diameter. Petalage is double with about 20 to 30 petals and about 2 to 4 petaloids irregularly arranged. When partially open, the bloom form is moderately ovoid to somewhat high centered to cupped, and the petals are loosely spiraled to somewhat undulated to cupped with petal edges moderately reflexed outward. When fully open, the bloom form is more cupped and the petals are loosely cupped to somewhat undulated with petal edges moderately reflexed outward.

PETALS

The substance of the petals is somewhat heavy and of medium thickness, with upper surfaces somewhat satiny and under surfaces slightly shiny. The petals are about 2.2 to about 3.8 cm. in length and about 1.7 to about 3.8 cm. in width at the widest point. Petal margins are entire.

The outer petals are nearly rounded to somewhat obovate in shape with rounded to sometimes mucronate apices.

The inner petals are moderately obovate in shape with rounded to sometimes mucronate apices.

Petaloids are about 0.7 to about 2.1 cm. in length and about 0.3 to about 0.8 cm. in width at the widest point. Petaloids are irregularly shaped moderately obovate to subulate with rounded apices.

NEWLY OPENED FLOWER

The under surface color of the outer, intermediate and inner petals is between 155D and 155B blushed with between 71C and 67A toward the petal edge. At the point where the petal attaches, there is a very small zone of near 4C. The upper surface color of the outer, intermediate and inner petals is between 155D and 155B blushed with between 71C and 67A toward the petal edge. At the point where the petal attaches, there is a small zone of near 4C.

The under and upper surface colors of the petaloids are similar in coloration to the upper and under surfaces of the intermediate and inner petals.

The general tonality of the newly opened flower is between 155D and 155B blushed with between 71C and 67A toward the petal edge.

THREE-DAY-OLD FLOWER

The under and upper surface color of the outer, intermediate and inner petals is between 155D and 155B blushed with between 71C and 67A toward the petal edge. There is no visible change in coloration at the point where the petal attaches.

The under and upper surface colors of the petaloids are similar in coloration to the upper and under surfaces of the intermediate and inner petals.

The general tonality of the three-day-old flower is between 155D and 155B blushed with between 71C and 67A toward the petal edge.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCIVE ORGANS

Stamens are average in number (average about 55) and are arranged regularly about the pistils; a few are mixed with petaloids. The filaments are of short length (about 0.3 to about 0.7 cm.) most with anthers. Filaments are between 5C and 6C in color. The anthers are of medium size for the class and all open approximately at the same time. Anther color when immature is near 22A on the external part and near 13D on the internal part. Anther color at maturity is near 164D on the external part and near 200A on the internal part. Pollen is moderate and between 20B and 18A in color.

FEMALE REPRODUCTIVE ORGANS

Pistils vary in number (average about 60). The styles are somewhat uneven, average to moderately long in length (about 0.3 to about 0.9 cm.), somewhat thin to average in caliper, and moderately separated. Stigma color is between 18B and 19C. Style color is between 154D and 150D usually heavily suffused with between 187A and 187B. Ovaries are usually all enclosed in the calyx. The ovaries are of medium size and between 158C and 159D in color.

Hips are of average length (about 1.6 to about 2.2 cm.), rounded in form with a flat top, and between 26A and 25A in color when ripe. The hip surface is smooth with thick fleshy walls. The sepals are fugacious and usually straight in shape.

The seeds are irregularly rounded, smooth in texture, approximately 7 to about 14 per hip, about 0.4 to about 0.6 cm. in diameter at the widest point and between 165D and 164A in color.

FOLIAGE

The compound leaves are usually comprised of three to nine leaflets and are borne abundantly. The seven-leaflets are about 8.2 to about 17.1 cm. in length and about 5.8 to about 13.2 cm. in width at the widest point, leathery to moderately crisp in texture on both sides, and glossy in finish on the upper side and slightly glossy in finish on the under side. The leaves have a pinnate venation pattern. The terminal leaflets are about 2.8 to about 8.8 cm. in length and about 2.2 to about 5.2 cm. in width at the widest point, shaped ovate to somewhat oval with acute apices and rounded bases. Their margins are usually simply serrate.

The upper surface color of the mature leaf is between 137A and 147A. The under surface color of the mature leaf is between 147B and 146B. The under and upper colors of the leaf veins on the mature leaf are similar in coloration to the upper and under surfaces colors of the mature leaf. The upper surface color of the young leaf is between 137C and 146B, often heavily suffused with between 187A and 187B. The under surface color of the young leaf is near 146B, often heavily suffused with between 187A and 187B. The under and upper colors of the leaf veins on the young leaf are similar in coloration to the upper and under surfaces colors of the young leaf.

The rachis is moderately heavy in caliper and rough. The upper side is somewhat shallowly grooved with very few hairs and few stipitate glands on the edges of the grooves. The under side of the rachis is rough with some stipitate glands and few small prickles. The rachis color is near 146D on the under side and near 137B on the upper side, sometimes lightly suffused on the young leaves with between 187B and 187C.

The stipules are about 1.0 to about 1.7 cm. in length and moderately wide (about 0.5 to about 1.0 cm.) with medium to somewhat long straight points that usually turn out at an angle of more than 45 degrees and sometimes recurve toward the stem. The under and upper surface color of the stipule is between 146B and 146C. The upper and under surfaces of the stipules are smooth in texture.

The petiole is moderately heavy in caliper and rough. The upper side is somewhat shallowly grooved with very few hairs and few stipitate glands on the edges of the grooves. The under side of the petiole is rough with some stipitate glands and few small prickles. The petiole is about 0.6 to about 1.8 cm. in length and about 0.1 to about 0.2 cm in width at the widest point. The petiole color is near 146D on the under side and near 137B on the upper side, sometimes lightly suffused on the young leaves with between 187B and 187C.

The plant displays an above average degree of resistance to powdery mildew (*Sphaerotheca pannosa*) and rust (*Phragmidium* sp.) as compared to other commercial varieties grown under comparable conditions in Pomona, Calif. The plant is cold hardy to zone 6 and heat tolerant to zone 10.

GROWTH

The plant has an upright moderately spreading medium height to somewhat tall growing habit (about 128 to about 175 cm. in height and about 122 to about 152 cm. spread at the widest point), with full branching. It displays vigorous growth and the canes are of medium caliper for the class (about 2.0 to about 2.9 cm. in diameter at the widest point).

The color of the major stems is between 146B and 146C. The major stems are rough in texture and they bear some large prickles that are about 0.6 to about 1.1 cm. in length. The large prickles are angled slightly downward with a medium length moderately narrow oval base; prickle color is between 166A and 165A. The major stem bears few small prickles of similar shape and coloration.

The color of the branches is between 137C and 148A. The branches are rough in texture and they bear some large prickles which are of similar size and shape to the large prickles on the major stems; prickle color is between 162A and 161A often moderately suffused with between 187C and 187D. The branches bear many small prickles of similar shape and coloration with many stipitate glands.

The color of the new shoots is between 137D and 148A often moderately suffused with between 187B and 187A. The new shoots are rough in texture and they bear few large prickles which are of similar size and shape to the large prickles on the major stems; prickle color is between 152C and 152D often heavily suffused with between 187B and 187A. The shoots bear many small prickles of similar shape and coloration with some stipitate glands.

I claim:

1. A new and distinct Grandiflora rose plant of the variety substantially as described and illustrated herein.

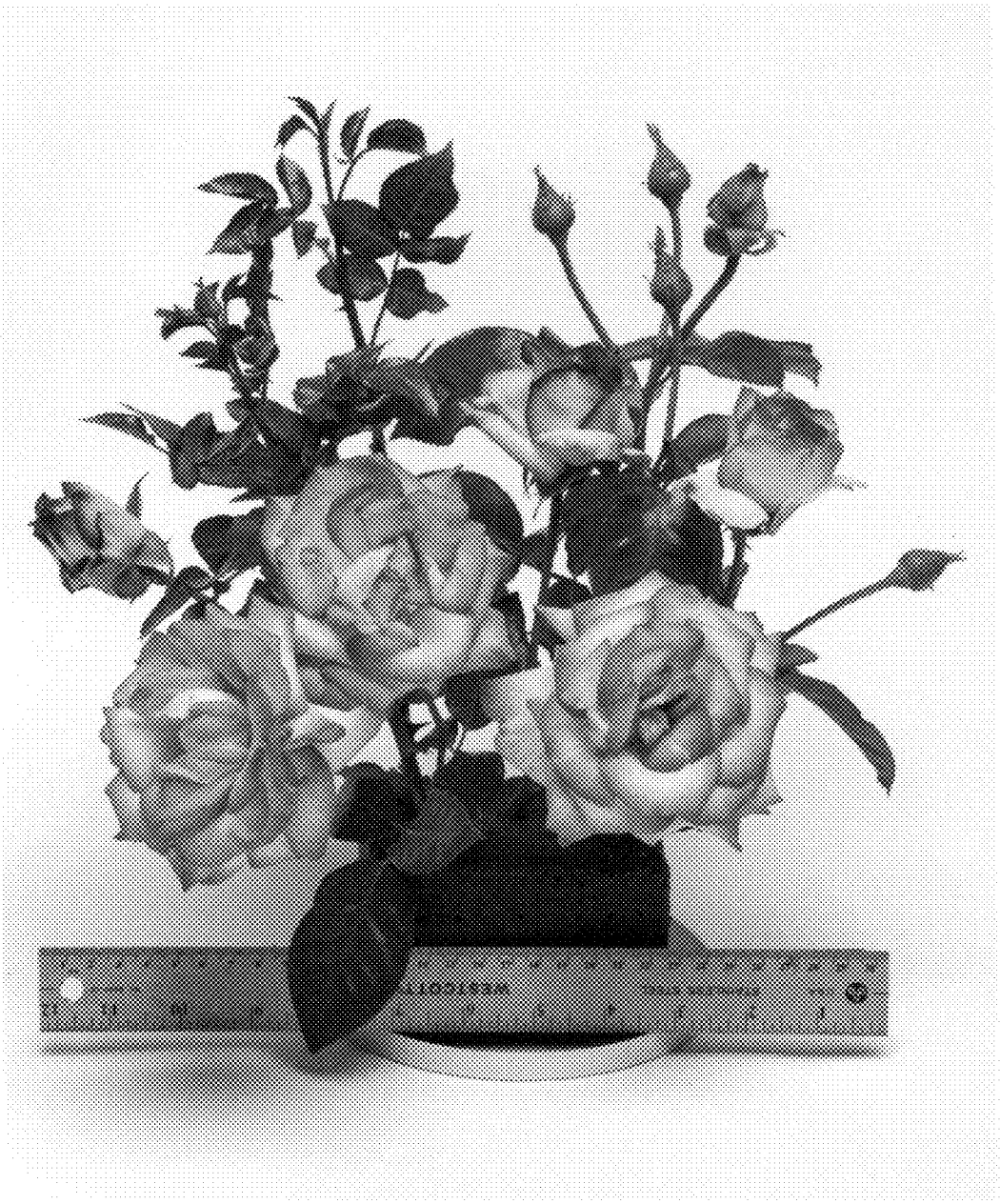

* * * * *